United States Patent [19]

Hull et al.

[11] Patent Number: 5,559,292
[45] Date of Patent: Sep. 24, 1996

[54] METHOD AND APPARATUS FOR THE IDENTIFICATION OF SPECIES

[75] Inventors: John B. Hull, Dore; Christian M. Langton, Doncaster, both of United Kingdom

[73] Assignee: University of Bradford, Bradford, United Kingdom

[21] Appl. No.: 256,484

[22] PCT Filed: Jan. 7, 1993

[86] PCT No.: PCT/GB93/00017

§ 371 Date: Oct. 12, 1994

§ 102(e) Date: Oct. 12, 1994

[87] PCT Pub. No.: WO93/14397

PCT Pub. Date: Jul. 22, 1993

[30] Foreign Application Priority Data

Jan. 7, 1992 [GB] United Kingdom .................... 9200218

[51] Int. Cl.⁶ ................................................ G01N 29/08
[52] U.S. Cl. .................. 73/597; 73/599; 73/646
[58] Field of Search ............... 73/579, 597, 599, 73/602, 629, 645, 646

[56] References Cited

U.S. PATENT DOCUMENTS

| | | | |
|---|---|---|---|
| 4,773,267 | 9/1988 | Abts | 73/597 |
| 5,255,564 | 10/1993 | Glad et al. | 73/597 |
| 5,305,239 | 4/1994 | Kinra | 73/602 |
| 5,433,112 | 7/1995 | Piche et al. | 73/597 |

FOREIGN PATENT DOCUMENTS

| | | |
|---|---|---|
| 0480554 | 4/1992 | European Pat. Off. . |
| 2221991 | 2/1990 | United Kingdom . |

OTHER PUBLICATIONS

"Ultrasonic pulse spectroscopy of a solid inclusion in an elastic solid" by F. Bifulco and W. Sachse, Ultrasonics, vol. 13 No. 3 May 1975 p. 113.

*Primary Examiner*—Hezron E. Williams
*Assistant Examiner*—Rose M. Finley
*Attorney, Agent, or Firm*—Edwin D. Schindler

[57] ABSTRACT

A method is disclosed for identifying the presence or concentration of a target species in a sample by transmitting a wave of ultrasonic vibration through the sample and calculating, from measured values for time of flight of the wave through the sample and its attenuation during that time, an identification parameter dependent on the type or concentration of the target species in the sample and independent of the distance travelled by the wave through the sample. The method is more convenient to use than existing identification techniques because of the removal of distance from the measurements and calculations necessary. The method is of particular use in identifying polymers, for example, in reclamation and recycling processes. An apparatus for performing the method is also disclosed.

28 Claims, 4 Drawing Sheets

METHOD AND APPARATUS FOR THE IDENTIFICATION OF SPECIES

FIELD OF THE INVENTION

This invention relates to a method for the identification of a target species in a sample, in particular a method which involves the use of ultrasonic vibrations. The invention also relates to apparatus for use in such a method.

BACKGROUND TO THE INVENTION

It is often necessary to identify the type and concentration of various species present in an unknown sample. This is especially so when it is desired to reclaim or recycle materials for re-use. In this case, it is necessary to be able to test a product to identify the presence of recyclable species in it and their relative concentrations.

When recycling materials, it is especially important to be able to detect the presence and concentration of contaminants which would otherwise adversely affect the recycling process. Even a small level of contaminant can often greatly affect the properties of a recyclable material. However, often the physical properties (including visual) of a likely contaminant are very similar to those of a target species to be recycled. For instance, polypropylene and polyethylene have very similar properties. It may be desired to recycle polypropylene from a product. A concentration of any more than about 1% of polyethylene contaminating that product can adversely affect the moulding and other properties of the recycled polypropylene.

Thermoplastic waste is also widely perceived to be a major environmental problem. Approximately 85% of the polymers used in the EC are thermoplastics and the volume of waste materials continues to rise commensurate with materials consumption. Attention has focused on the economic treatment and disposal of waste materials from both commercial and domestic products, including packaging, white goods, scrapped automotive components and textiles.

Reclamation of plastics compositions and recycling of polymeric materials is of increasing interest to the industrial sector which includes materials waste collectors and separators, materials processors, product users, materials suppliers and processing equipment suppliers. However, with the inherent limitations in current identification and separation technology, it is inevitable that a relatively high percentage of recycled materials will contain contaminants.

Plastic bottle collection and recycling has also made considerable advances in recent years. However, to date sorting of PET (polyethylene terephthalate), PVC (polyvinyl chloride) and PE (polyethylene) bottles has been achieved mainly by hand, using unskilled labour. It is imperative that the reclaimed PET does not contain PVC, as a contaminant, in amounts greater than 50 ppm, because this results in the formation of low molecular weight degradation products which make processing of the material extremely difficult to control and can result in serious impairment of mechanical properties. In addition, the reclamation process can result in partial depolymerisation of the PET which also causes major processing problems.

In the UK, most plastics waste (90%) is disposed of in landfill sites, where it is hoped that the inert nature of plastics will have no long term harmful effects. Until recently, this approach was viewed as the optimum method of plastics waste disposal by the Waste Management Sector. However, rising costs per tonne of plastic disposed of in landfill has promoted a search for more economical solutions.

Incineration with energy recovery has been postulated as an alternative way of dealing with the waste problem. This approach, however, is viewed by many as both wasteful of a diminishing natural resource and environmentally unfriendly because of the potential impact of gas emissions. Another option is to recycle and reuse plastic waste directly.

Direct reclamation is thus increasingly viewed as the best approach to retaining the many benefits of plastics whilst minimising the impact associated with waste disposal.

However, increasing use of a wider range of thermoplastics and polymer blends with additives has made the identification and separation of waste materials and components a difficult, expensive, labour-intensive task. Moreover, at present little knowledge exists regarding the effects of recycling, and in particular, multiple recycle/processing stages on the properties of polymeric materials. The former problem reduces the cost effectiveness of producing recycled materials whilst the latter problem inhibits use of recycled materials by product manufacturers.

It is inevitable that materials currently recycled will contain contaminants, because of the inherent limitations in separation technology. For example, in reclamation of plastics materials from granulated automotive components, flotation or hydrocyclone processes should remove PVC and ABS (acrylonitrile butadiene styrene), but cannot separate PP (polypropylene) and HDPE (high density polyethylene) because they have similar densities.

Essentially, it is necessary to deal with a somewhat variable blend rather than a single homopolymer. This creates major problems for the plastics processor, because of the resultant variability in processing characteristics. In addition, PP and HDPE are incompatible, and particles of HDPE dispersed in a matrix of PP result in reduced component stiffness and creep resistance, as well as altering melt rheology.

Various methods are currently available for the identification of species in unknown samples. X-ray fluoroscopy is one such method. However, this is an expensive and inherently unsafe technique, requiring the use of protective screen systems and highly skilled operators. Moreover, its use is restricted to identifying the presence of ionic or polar species. For instance, it may be used to identify polymers such as PVC, but not electrically neutral species.

A very extensive database is needed for use with X-ray fluoroscopy if its results are to be meaningful. This database must include data for each target species which a user is likely to need to identify, for mixtures of such species and also for samples containing pigments (such as, for example, titanium oxide, used to impart a white colour) of different types and/or concentrations.

For the purposes of recycling, some target species (especially metals) can be separated from contaminants by a melting process. This technique can be used where the various species present in a sample all have different melting points; some melt before others and can thus be separately removed from the sample. However, this technique is of no use in identifying and separating polymers, which will often react with one another at or before their melting points.

Chemical reaction techniques may be used to identify some types of species from a sample. Again, however, such techniques are generally of no use for the identification and separation of polymers, the reactions of which are usually too complex to be of practical use.

Other techniques have been developed to assist in the identification and separation of plastic waste, including moulded-in codes, X-ray spectroscopy, and FT infra-red spectroscopy. However, none of these methods of approach has proved to be either completely satisfactory or acceptable to a wide proportion of the industrial waste management sector.

Moulding in bar codes seems to be the simplest, most cost effective method of approach, but this solution suffers from the possibility that in-use damage of the label would render the code unreadable. X-ray spectroscopy is a fast, reliable technique for identifying specific atomic species, such as Cl in PVC. However, the system is relatively expensive and is limited in application. It would be impossible, for example, to differentiate between PP and PE. Infra-red spectroscopy is a highly sensitive technique which can be used for detecting very small quantities of contaminant (less than 0.1 gms) in a given material. However, this approach is also expensive, and cannot easily be used on-line, because only thin film specimens can be scanned. Essentially, samples need considerable preparation prior to analysis.

Thus, there is currently much demand for the efficient separation and recycling of polymers, and yet none of the currently available techniques seems satisfactorily to meet this demand.

Ultrasonic vibrations have been used in the past to identify structural properties of certain materials. For instance, metallurgists have used ultrasound to detect the presence and geography of defects such as cracks in metals and certain polymers. These defects interrupt the passage of vibrations through the material. Such a technique has also been used in the past to study bone fractures.

Ultrasonic vibrations have not, however, been used in the past to identify a particular species in an unknown sample. There are several possible reasons for this. Every species (for instance, a chemical element, compound, alloy or mixture) will have a discrete value for the velocity at which sound waves may propagate through that species. Theoretically, therefore, it would be possible to identify a species by passing ultrasonic vibrations through a sample containing the species and measuring the time of flight for the vibrations through the sample. However, because the time of flight depends on both velocity and distance, the exact distance which the sound waves travelled through the species would also need to be measured. This distance would often be a difficult parameter to measure, particularly in the case of amorphous samples or samples of unusual shape. It would also be an impractical parameter to measure for samples in which the exact position and/or quantity of the target species within the sample were not known. For these reasons, the use of ultrasonic vibrations to identify species has until now been regarded as unacceptably impractical for use on a commercial scale.

Also seen to be a problem with the use of ultrasound is attenuation of the vibrations by the sample through which they are transmitted. Whilst on the one hand the higher the frequency of the vibrations, the higher the resolution in the transmitted signals to be analysed, on the other hand, increased frequency also increases the amount of attenuation of the vibrations. This attenuation, of the strength of ultrasonic vibrations as they pass through a sample, makes the vibrations more difficult to detect and analyse. It has historically been seen as prohibitive to the effective use of ultrasound for commercial identification purposes.

It is therefore an aim of the present invention to provide a method and apparatus for the identification of a target species in a sample, which overcome at least mitigate the above described problems with conventional methods and apparatus. They should preferably be of use for a wide range of different species types, and relatively easy, safe and inexpensive to use.

STATEMENT OF THE INVENTION

According to the present invention there is provided a method of identifying the presence and/or concentration of a target species in a sample, comprising the steps of:

1. transmitting a wave of ultrasonic vibration of known strength through the sample;
2. receiving and measuring the strength of the transmitted wave, or its reflection, after its passage through the sample;
3. measuring the time of flight of the wave through the sample, between transmission of the wave and its reception;
4. calculating the attenuation of the strength of the wave during its time of flight;
5. calculating from the values for time of flight and attenuation an identification parameter dependent on the type and/or concentration of the target species in the sample and independent of the distance travelled by the wave through the sample; and
6. comparing the calculated identification parameter with known identification parameters for known types and/ or concentrations of species, so as to identify the presence and/or concentration of the target species in the sample.

The theory behind the method of the invention is as follows. Attenuation of the strength of an ultrasonic vibration of a particular frequency f, by a material through which the vibration passes, is usually measured in decibels (dB). It is the product of the attenuation per unit length, $\alpha$, for the material (a property of the material itself, which will have a discrete value for each different material) and the distance d which the vibration travels through the material.

The time of flight, t, for the vibration, ie: the time taken for it to pass through distance d in the material, is equal to distance d divided by the velocity v with which the vibration travels through the material. Again, this velocity is a property of the material and will have a discrete value for each different material.

Thus, it is possible to define a parameter, S, which is the measured attenuation A, divided by the time of flight t, and is a property of the material through which a vibration passes, independent of the distance which the vibration travels. The removal of distance from the calculation is a great advantage, since this is usually a parameter which is extremely difficult to measure in commercial situations.

The identification parameter S at any particular frequency f is thus defined by the equation:

$$S = \frac{A}{t} = \alpha \, d \cdot \frac{v}{d} = \alpha v$$

It is likely to have a unique value for each different species or at least a unique spectrum of values over a range of different frequencies of ultrasonic vibration.

The identification parameter in the method of the invention is preferably calculated in this way, ie: by dividing the attenuation of the wave strength by the measured time of flight. The resulting identification parameter, S, will have units of dB s$^{-1}$.

More preferably, an index parameter is also calculated from the identification parameter S. The index parameter is given by the formula $$\frac{\Delta A}{\Delta ft} = \frac{\Delta S}{\Delta f}$$

where f is the frequency (of the ultrasonic vibration) at which the method of the invention has been used, and the parameter S calculated, for a given sample. The index parameter, having units of dB MHz$^{-1}$s$^{-1}$ where f is in MHz, is a form of numerical "signature", entirely dependent on the nature of the target species which it characterises.

The index parameter is effectively the gradient of the graph of attenuation vs frequency for any particular sample, preferably measured in a range of the graph in which the relationship of A and f is substantially linear (portions of the graph, particularly at low and high frequencies, will include noise, dependent on the properties of the transducer used, which adversely affects the calculation of the index parameter). Use of the index parameter as well as the identification parameter S, both being entirely independent of the distance which the ultrasonic vibrations travel through the sample, greatly increases the accuracy of the method of the present invention.

Since the increase of attenuation with frequency is usually not completely linear, it is also possible to calculate a further parameter (deviation parameter) from results taken using the method of the invention. The deviation parameter, a measure of the non-linearity of the A vs f graph, is defined as the maximum deviation of the profile from a linear relationship, and may be calculated using a standard linear regression technique. It is preferably expressed as a percentage. Its value will also differ between target species; thus, together with the identification parameter and the optional index parameter, the deviation parameter may be used accurately to identify any target species, and in particular to differentiate between species which have similar identification parameters.

The deviation parameter may alternatively be calculated as a measure of the non-linearity of the graph of identification parameter S vs frequency f.

Because distance is eliminated from the equation, the size and shape of the sample in which the target species is to be identified is not critical to the efficient operation of the method of the invention. No sample preparation is needed prior to transmission of the ultrasonic vibration through the sample. Moreover, the method of the invention is relatively simple, safe and rapid to use, and is also non-invasive. It allows the use of ultrasound to identify species in a sample, where previous thinking would have dismissed such a possibility as impractical.

The target species may be virtually any type of material, for instance a metal or other chemical element or a polymer (including a textile polymer) or other compound. The method of the invention is especially useful for identifying the presence and/or concentration of a polymer in a sample, particularly for the purposes of reclamation and recycling of the polymer. Examples of polymers which could be identified in this way include perspex, polystyrene, polyethylene and polypropylene.

The method may be used to identify a single species, or a mixture of different species, or an alloy or copolymer. In most cases, it can produce accurate results even at relatively low concentrations of the target species.

Preferably, a series of identification parameters is calculated for the target species, each being calculated using a different frequency of ultrasonic vibration in the method. The frequency of the vibration will affect the measured attenuation in strength of the ultrasonic wave and thus also the value of the identification parameter. In this way, the method can be repeated on the same sample using a range of different vibration frequencies, and a spectrum of identification parameters built up. This spectrum will be unique for the particular target species type and concentration in the sample under investigation. Calculation of a series of, rather than a single, identification parameter thus allows more accurate identification of any particular target species. It also allows calculation of an index parameter, as described above.

The wave of ultrasonic vibration is preferably transmitted through the sample by means of an ultrasonic transducer, examples of which are commonly available. The transducer is preferably of the "broad band" type, capable of delivering ultrasonic vibrations of a range of different frequencies.

The transducer is preferably placed in direct contact with the sample. This makes the method of the invention particularly convenient, simple and quick to use. Alternatively, the transducer may be coupled to the sample, for instance through an appropriate oil or a bath of water or other fluid surrounding the sample.

Typically, the transducer will be used in combination with an electronic pulser, which will excite the transducer to produce a series of ultrasonic waves at a desired frequency. Such pulsers are well known and commonly available. In this particular case, the preferred type is an analogue pulser.

The wave of ultrasonic vibration is preferably received by means of another transducer. Conventional equipment can be used to process signals received by this transducer, and thus measure (and usually also display and/or record) the strength of the received wave. A digital receiver, for example, may be used for this purpose.

The sample may be of any thickness, since sample thickness does not affect the value of the calculated identification parameter. A thin film of sample, of the order of a few micrometers thick may, for instance, be investigated using the method. The sample may equally be in the form of a powder, suspension or solution. The sample need not necessarily be cleaned or pre-prepared in any way prior to use in the method.

The attenuation of the wave strength, and the identification and other parameters, are preferably calculated by means of a computer.

The known identification parameters with which the calculated parameter is compared are preferably stored on a computer database. This may contain, for example, standard identification, index and/or deviation parameters for a number of different types of species at a range of different concentrations. The database will preferably include calibration spectra, one for each species of interest, showing the variation of the identification parameter for that species with the frequency of ultrasonic vibration passing through a sample containing the species. It may include standard index parameters for various target species of interest. The database may also include spectra showing the variation of the identification parameter for a particular species with its concentration in a sample. These latter spectra will be of particular use for identifying a target species in a sample containing a mixture of species, for detecting the presence of contaminants in a sample, or for identifying a target mixture.

The ultrasonic wave is preferably transmitted so as to pass straight through the sample. This is known as operating the method in its "transmission" mode. The transmitted wave is then received, and its strength measured, on the opposite side of the sample as the wave exits the sample.

Alternatively, the transmitted wave may be received, and its strength measured, at or near the source from which it is transmitted. In this way, the wave is allowed to pass through the sample and to be reflected back towards its source by species present in the sample. The time of flight for the wave is in this case equal to the time taken for its passage through the sample in both directions, ie: the time which elapses between transmitting the wave and receiving its reflection. The time of flight and the attenuation of the wave strength are then more or less double what they would be if the transmitted wave were simply received as it left the sample.

In this latter version of the method (known as the "pulse-echo" mode of operation), the transmitted wave, following reflection, is preferably received by means of the same transducer which is used to transmit the wave.

When the method of the invention is used in its transmission mode, the orientation of the sample, relative to that of the ultrasonic wave, will usually need to be adjusted to allow efficient reception and measurement of the transmitted wave. However, when the method is operated in its pulse-echo mode, the orientation of the sample is irrelevant.

Ultrasonic vibration is preferably transmitted through the sample at a frequency less than or equal to 2.5 MHz. The wave of vibration may be a compression wave (ie: longitudinal) or a shear wave (transverse). In general, the use of compression waves is preferred since these tend to have lower transmission speeds. The two types of wave (ie: compression and shear) will each give a different value for the identification parameter for a particular type and concentration of target species. Thus, the method of the invention may be performed twice, once using a compression wave and once using a shear wave, to provide a yet more definitive identification of the presence and/or concentration of the target species.

According to the invention there is additionally provided apparatus for identifying the presence and/or concentration of a target species in a sample, the apparatus comprising:

1. means for transmitting a wave of ultrasonic vibration of known strength through the sample;
2. means for receiving and means for measuring the strength of the transmitted wave, or its reflection, after its passage through the sample;
3. means for measuring the time of flight for the wave through the sample, between transmission of the wave and its reception;
4. means for calculating the attenuation of the strength of the wave during its time of flight; and
5. means for calculating from the values for time of flight and attenuation an identification parameter dependent on the type and/or concentration of the target species in the sample.

The means for transmitting the wave of ultrasonic vibration is preferably a transducer, more preferably a broad band transducer. The means for receiving the transmitted wave is preferably also a transducer. A single transducer may function as both the means for transmitting the wave and the means for receiving the transmitted wave once the latter has passed through the sample and been reflected back to the transducer.

The means for calculating the attenuation in the strength of the wave, and/or the means for calculating the identification parameter, is preferably a computer.

The apparatus preferably additionally comprises a database of known identification parameters, for known types and/or concentrations of species, with which an identification parameter calculated using the apparatus may be compared. This database is preferably a computer database.

The present invention will now be described by means of the following examples and with reference to the accompanying illustrative drawings of which:

DETAILED DESCRIPTION

In recent years, member states within the EEC have given considerable thought to the recovery of thermoplastic waste from both the commercial and domestic environments. Reclamation of waste products from scrapped cars, white goods and disposable packaging has received particular attention. However, the increasing use of a wide range of different polymer types and polymer blends has made the identification and separation of waste materials and components a difficult if not impossible task.

Although a number of techniques such as visual/optical examination (bottle sorting) and x-ray fluoroscopy (PVC-Cl species analysis) have been devised, only limited success has been achieved.

The method of the present invention is, in contrast, reliable, economic and capable of being "tailored" for a wide range of different requirements and applications.

Figure 1:
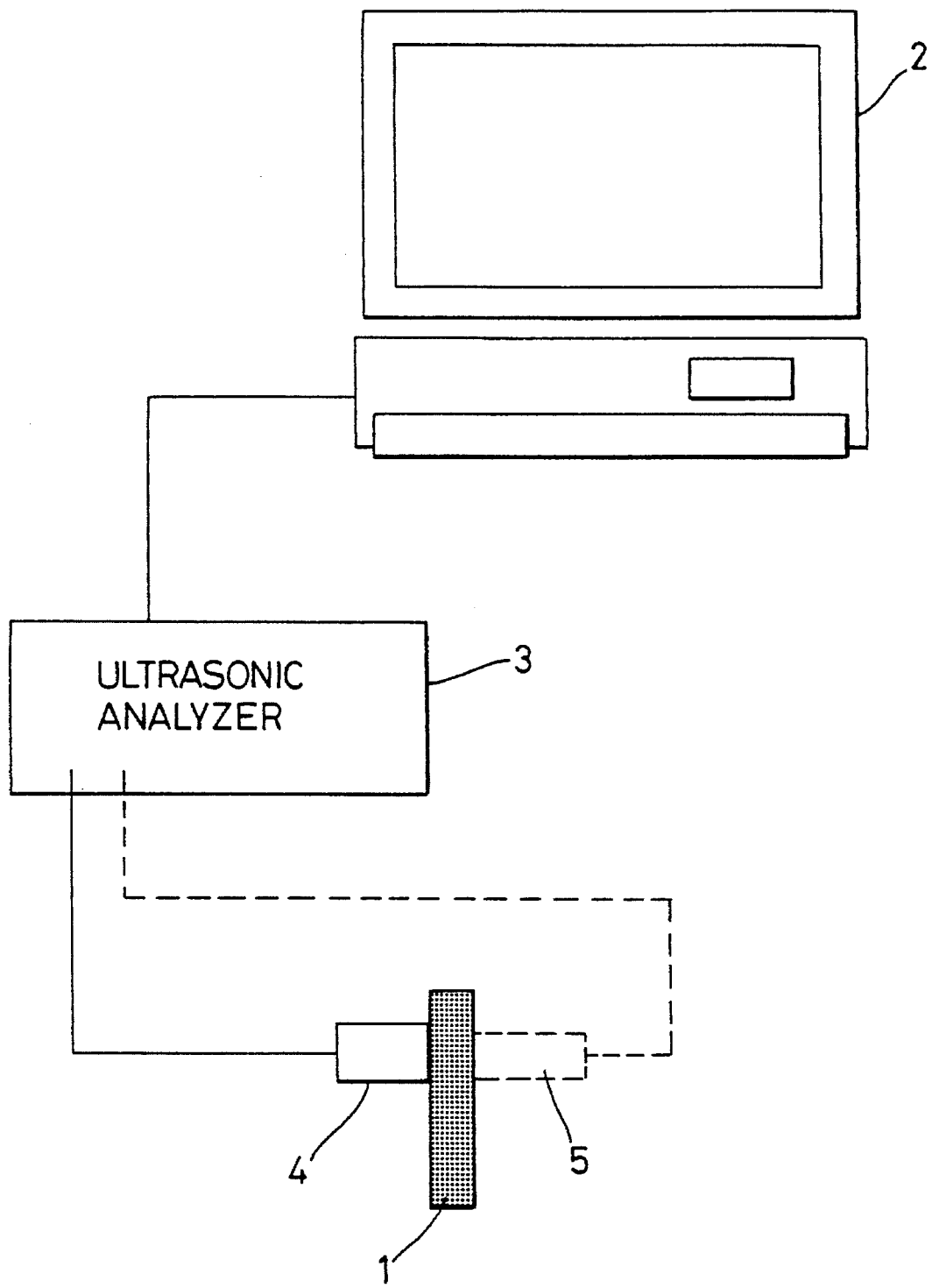
FIG. 1 shows schematically apparatus in accordance with the invention.

The technique, described here as an example of the method of the invention, employs a digital ultrasonic analyser for variable frequency pulse-echo/through transmission analysis, coupled to either one or two broadband ultrasonic transducers. A schematic diagram of a typical experimental set up is shown in FIG. 1. Analysis of the ultrasonic properties of a sample 1 is facilitated by an integral digital computer 2 using customised system software. 3 is the ultrasonic analyser, capable of either pulse-echo or through transmission analysis, and 4 one of the transducers. The second transducer, 5, is needed only if the method is used in the through transmission mode; in the pulse-echo mode, only the single transducer 4 is used. The two transducer "probes" 4 and 5 are broadband ultrasonic transducers, of 1 MHz nominal frequency.

The sample 1 might typically be a polymeric specimen.

The approach adopted precludes the necessity of measuring sample dimensions. Analysis yields a specific HL (HL= Hull/Langton) index or signature which can be compared against a known database for identification of a target species. Polymers especially can be identified in this way. For example, PVC or PET transparent bottles can easily be distinguished. Resolution can be improved by taking measurements using both compressive wave velocity ($V_c$) and shear wave velocity ($V_s$) over a range of frequencies, and it is possible to identify homopolymers, co-polymers and polymer blends.

EXAMPLE 1

A range of polymeric components/materials was tested using the ultrasonic identification technique of the invention in order to show how the method could be applied in practical situations. In the following examples, attenuation vs broadband frequency (DC–2.5 MHz) scans were taken from a number of areas of each sample. The results are presented as a HL (Hull/Langton) index given by:

$$HL = \frac{A}{f} \times \frac{1}{t} = \frac{A}{ft} \quad dB\ MHz^{-1}\ s^{-1}$$

Where f=Frequency range of analysis (MHz);

A=measured attenuation of ultrasound passing through the sample (dB); and t=time of flight of ultrasound through the sample (s).

The HL index is a calculated index parameter (numerical signature) for any particular species.

Figure 2:
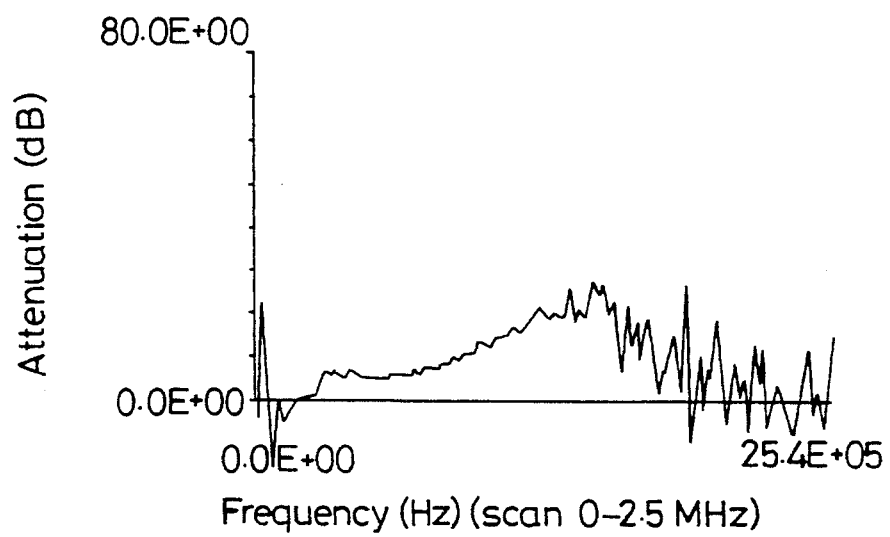
FIGS. 2 and 3 show typical data obtained using a method in accordance with the invention to scan a nylon sample over a range of ultrasound frequencies.
Figure 3:
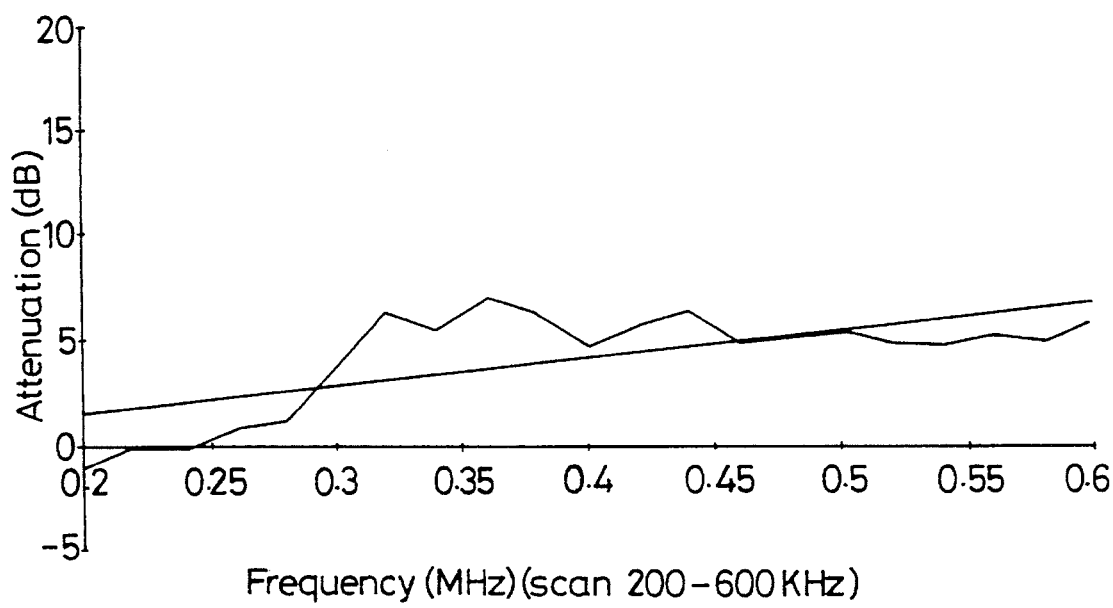

FIGS. 2 and 3 show typical data obtained during broadband scanning of a nylon sample over the frequency ranges 0–2.5 MHz, and 200–600 KHz, respectively (graphs show attenuation (dB) vs frequency (Hz and MHz respectively)).

Figure 4:
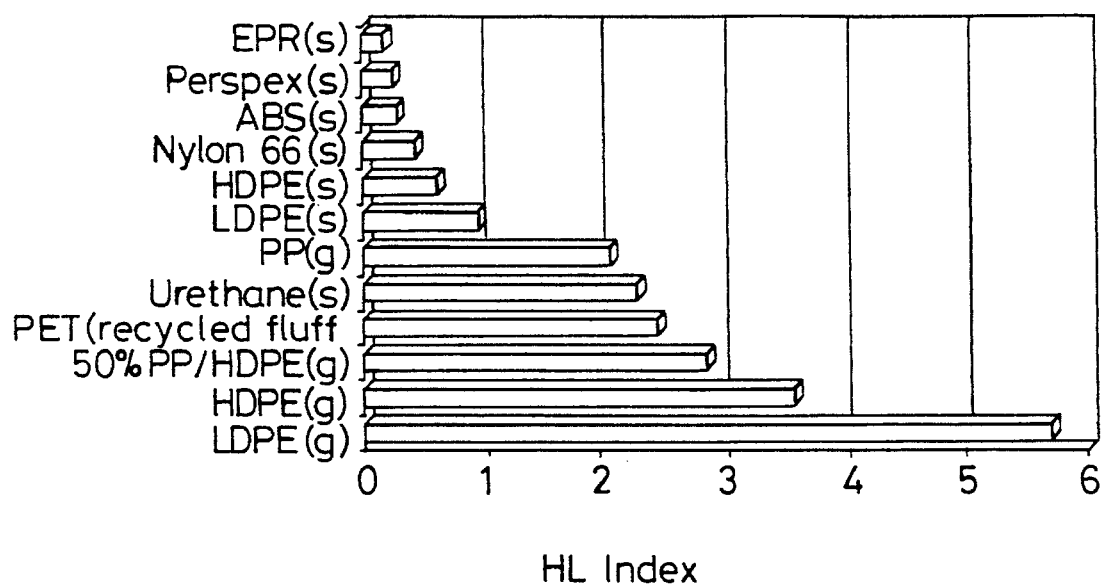
FIG. 4 shows the HL index values for a number of different polymers, obtained using a method in accordance with the invention.

Table 1 and FIG. 4 depict the relative HL indices for a range of different polymers scanned in a variety of base conditions, ie, solid, granulated or fluff (reclaimed) form. In addition to the marked differences between the HL indices of the polymers scanned ultrasonically, a second variable was clearly in evidence, ie, the maximum deviation of the attenuation/frequency profile from a linear relationship. This should provide a secondary method of polymer characterisation, particularly when scanning different materials with similar HL indices. The HL index and the maximum deviation can together be used accurately to identify the presence of a particular target species in an unknown sample.

TABLE 1

| Species (s = solid; g = granulated) | HL Index dB MHz$^{-1}$ s$^{-1}$ | Non Linear Profile Maximum % Deviation |
|---|---|---|
| 1) LDPE (s) (low density polyethylene) | 1.003 × 10$^6$ | ±1% |
| 2) HDPE (s) (High density polyethylene) | 0.656 × 10$^6$ | ±4% |
| 3) Nylon 66 (s) | 0.465 × 10$^6$ | ±25% |
| 4) EPR (s) (Ethylene propylene rubber) | 0.212 × 10$^6$ | ±6% |
| 5) Perspex (s) | 0.284 × 10$^6$ | ±10% |
| 6) Urethane foam (s) | 2.33 × 10$^6$ | ±9% |
| 7) HDPE (g) | 3.6 × 10$^6$ | ±8% |
| 8) LDPE (g) | 5.7 × 10$^6$ | ±6% |
| 9) PP (g) (polypropylene) | 2.1 × 10$^6$ | ±47% |
| 10) PP/HDPE (g) 50/50 | 2.9 × 10$^6$ | ±26% |
| 11) ABS (s) | 0.312 × 10$^6$ | ±10% |
| 12) PET (recycled) (fluff) | 2.5 × 10$^6$ | ±10% |

All granulated samples were tested by compacting the granules with water to fill in the interstices, and hence to provide good ultrasonic contact.

Non-Linearity of Ultrasound Attenuation Profile

The increase in ultrasound attenuation A with frequency f for any material follows the relationship $$A = k.f^n$$

where k is a constant. The value for n typically varies between 1.0 for most solids and 2.0 for most liquids.

In the assessment of broadband ultrasonic attenuation (BUA), it is possible to plot attenuation A as a function of frequency f and express the BUA index as the regression slope. With n addition, however, the variation in linearity about this regression may be utilised as a measurement parameter. The non-linearity may be expressed as the percentage ratio of the deviation in the regression slope divided by the mean value for the regression slope. Work to date suggests that a significant cause of this non-linearity is a complex interaction between the excitation by the ultrasonic wave and the structure of the material. For example, semicrystalline PE demonstrates a highly linear relationship, whereas fully crystalline PP demonstrates a high degree of non-linearity.

The deviation of the average HL index from linearity is a further indication of the sensitivity of the technique to the ultrasonic property differences between various materials. This deviation represents, for each material, the maximum difference at any point along an attenuation vs frequency plot from the gradient (dA/df) dB MHz$^{-1}$.

In effect, this parameter represents an additional means of identification of polymeric materials from a random batch of samples with relatively similar HL indices.

Further Experiments

Figure 5:
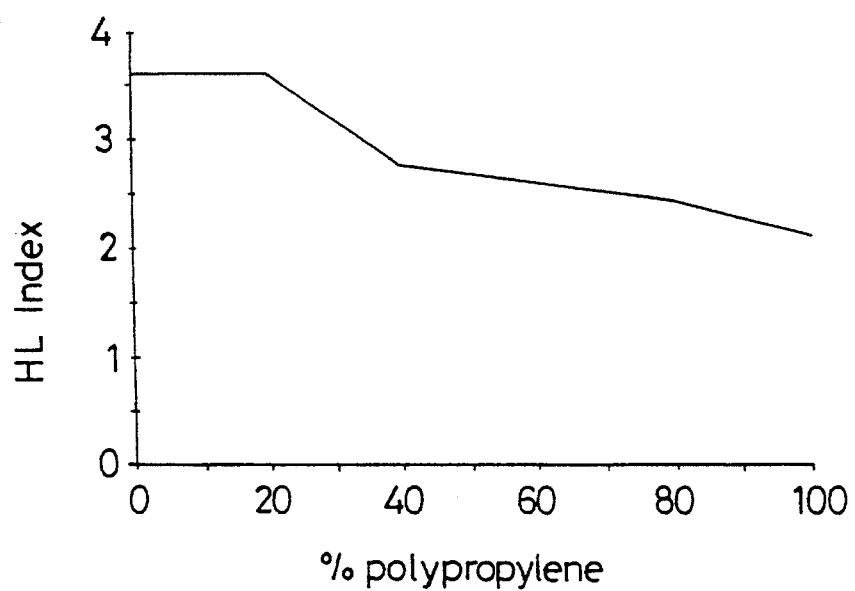
FIG. 5 shows how the HL index varies with percentage of polypropylene in a sample.

In a further experiment, polypropylene and high density polyethylene (HDPE) mixes were prepared from granulated polymers ranging from 0% to 100% polypropylene, compressed and confined into a thin walled tube (20 mm in diameter) and scanned ultrasonically using the method of the present invention. This method allows the effects of the tube to be obviated. The relationship of the HL index versus the percentage of polypropylene is shown in FIG. 5. Available evidence suggests a nearly linear relationship between the ultrasonic characteristics of the blends, as measured by the HL index, and the percentage of polyethylene.

Sensitivity of Ultrasound Analysis

Figure 6:
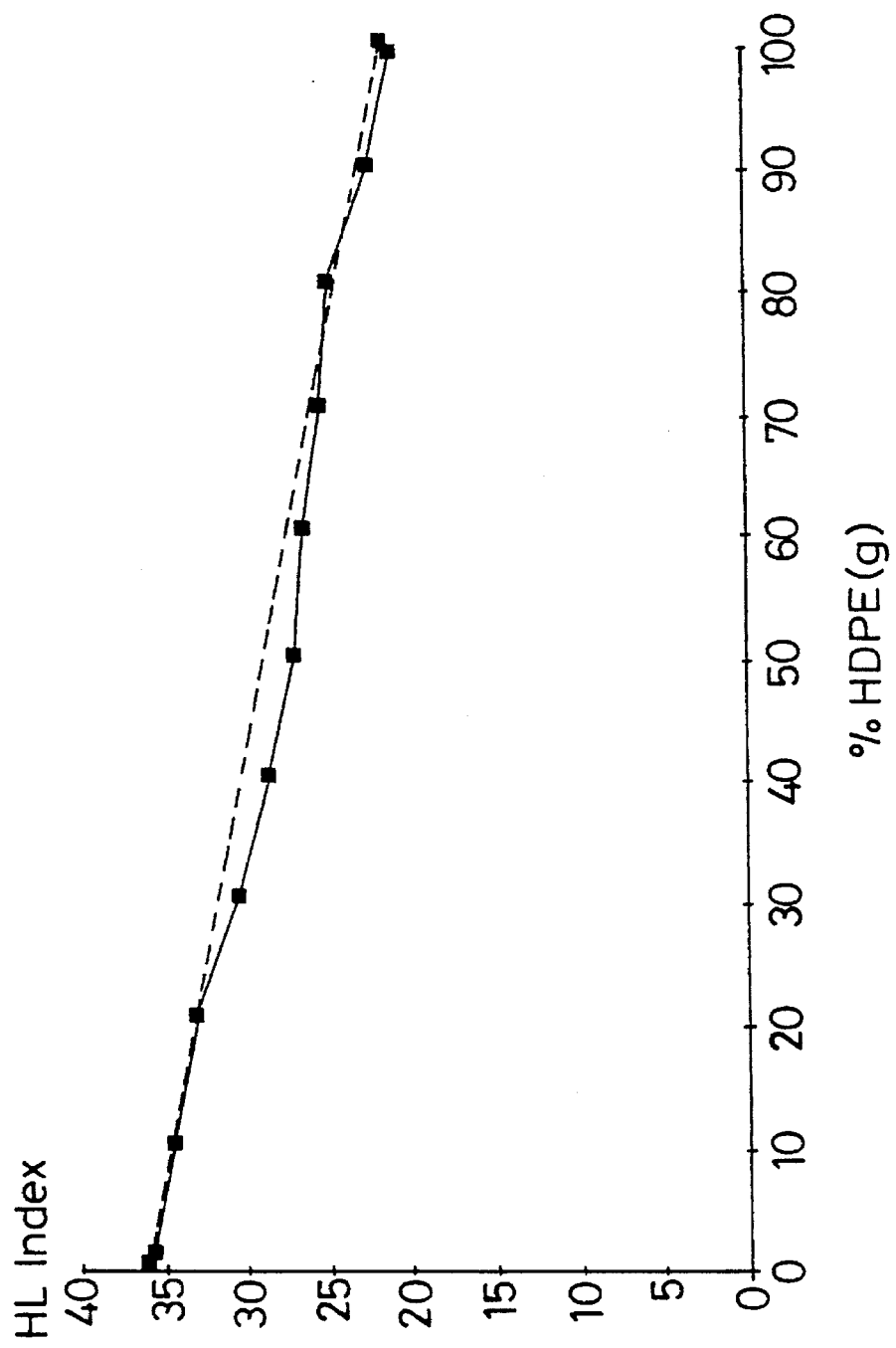
FIG. 6 shows how the HL index varies with percentage of granulated high density polyethylene (HDPE) in a sample.

FIG. 6 (a graph of HL index vs percentage of granulated HDPE in PP/HDPE mixes) provides further evidence of the sensitivity of the HL index analytical approach. A distribution of either 1% PP in HDPE or 1% HDPE in PP can be readily resolved, despite the relatively crude nature of the test material type (coarse granulated base materials). Although some deviation from linearity is apparent at relatively high concentrations, such concentrations are of no commercial importance.

Conclusions

The conclusions which can be drawn from the above described work are as follows:

1. The method of the present invention offers a cheap, reliable method of identification of species, in particular of waste polymeric materials/components for reclamation and recycling both on and off line. In addition, by comparison with X-ray fluoroscopy techniques, the method of the invention is inherently safe.

2. Computer assisted comparison of measurements taken using the method, against an extensive database of ultrasonic properties of known materials, should allow identification of homopolymers, co-polymers and polymer blends, and even additive types, such as pigments or reinforcing agents.

3. Evidence suggests that both solid components and granulated polymers can be identified.

4. It has also been found that for a particular target species at a particular ultrasonic frequency, the value of the HL index remain constant regardless of the distance over which the ultrasound has to travel through the sample, thus making the HL index an extremely useful identification parameter.

5. The uses of the method and apparatus of the invention are likely to be wide ranging and include, for example, reclamation and recycling of waste materials, the treatment of waste water (in particular industrial waste water), etc. . .

What is claimed is:

1. A method for identifying the presence or concentration of a target species in a sample, comprising the steps of:
   a. transmitting a wave of ultrasonic vibration of known strength through the sample;
   b. receiving and measuring the strength of the transmitted wave, or a reflection of the wave, after passage of the wave through the sample;
   c. measuring the time of flight of the wave through the sample, between transmission and reception of the wave;
   d. calculating the attenuation of the strength of the wave during a time of flight of the wave;
   e. calculating from values for the time of flight and attenuation, an identification parameter dependent on the type or concentration of the target species in the sample and independent of the distance travelled by the wave through the sample; and,
   f. comparing the calculated identification parameter with known identification parameters for known types or concentrations of species, for identifying the presence or concentration of the target species in the sample.

2. A method according to claim 1, wherein the identification parameter is calculated by dividing the attenuation of the strength of the wave during its time of flight of the wave by the measured time of flight.

3. A method according to claim 1, further comprising repeating steps (a)–(e) on the sample at a number of different frequencies f of the transmitted wave of ultra-sonic vibration, for calculating a number of corresponding identification parameters, the method additionally comprising the steps of calculating from the identification parameters an index parameter proportional to the change in the identification parameter divided by the corresponding change in the frequency of the transmitted wave over the range of frequencies at which the method is carried out; and comparing the calculated index parameter with known index parameters for known types or concentrations of species, for identifying the presence or concentration of the target species in the sample.

4. A method according to claim 3, wherein the index parameter is calculated as the gradient of the graph of attenuation of wave strength vs vibration frequency over the range of frequencies at which the method is carried out, in a region of the graph in which the relationship of attenuation and frequency is substantially linear.

5. A method according to claim 3, additionally comprising the steps of calculating from a graph of attenuation vs frequency a deviation parameter, defined as the maximum deviation of the graph from a linear relationship; and comparing the calculated deviation parameter with known deviation parameters for known types or concentrations of species, for identifying the presence or concentration of the target species in the sample.

6. A method according to claim 3, additionally comprising the steps of calculating from a graph of the identification parameter vs frequency over the range of frequencies at which the method is carried out a secondary deviation parameter, defined as the maximum deviation of the graph from a linear relationship; and comparing the calculated secondary deviation parameters for known types or concentrations of species, for identifying the presence or concentration of the target species in the sample.

7. A method according to claim 3, additionally comprising the steps of generating a spectrum showing the variation of the calculated identification parameter with the frequency of vibration at which the method is carried out; and comparing the generated spectrum with known spectra for known types or concentrations of species, for identifying the presence or concentration of the target species in the sample.

8. A method according to claim 1, wherein the target species is a polymer.

9. A method according to claim 1, wherein the target species is a mixture of two or more species.

10. A method according to claim 1, wherein the target species comprises an alloy or copolymer.

11. A method according to claim 1, wherein the wave of ultrasonic vibration is transmitted through the sample by means of an ultrasonic transducer.

12. A method according to claim 11, wherein the transducer is of the "broad band" type.

13. A method according to claim 11, further comprising the step of placing the transducer in direct contact with the sample.

14. A method according to claim 11, further comprising the step of coupling the transducer to the sample via a fluid surrounding the sample.

15. A method according to claim 1, wherein the wave of ultrasonic vibration is received by means of a transducer.

16. A method according to claim 1, wherein the transmitted ultrasonic wave is received, and the strength of the wave measured, on the opposite side of the sample to that from which the wave was transmitted, as the wave exits the sample.

17. A method according to claim 1, wherein transmitted wave is received, and the strength of the wave measured, at or near the source from which the wave is transmitted, following passage of the wave through the sample and reflection of the wave back towards the source by the species present in the sample.

18. A method according to claim 17, wherein the transmitted wave, following reflection, is received by means of the same transducer for transmitting the wave.

19. A method according to claim 1, wherein the frequency of the wave of ultrasonic vibration is less than or equal to 2.5 MHz.

20. A method according to claim 1, wherein the wave of ultrasonic vibration is a compression wave.

21. A method according to claim 1, in which steps (a)–(f) are performed on the sample once using a compression wave of ultrasonic vibration and once using a shear wave of ultrasonic vibration; and further comprising the step of comparing the calculated identification parameters with known identification parameters obtained, using compression and shear waves respectively, for known types or concentration of species, for identifying the presence or concentration of the target species in the sample.

22. Apparatus for identifying the presence or concentration of a target species in a sample, the apparatus comprising:
   a. means for transmitting a wave of ultrasonic vibration of known strength through the sample;
   b. means for receiving and means for measuring the strength of the transmitted wave, or a reflection of the wave, after passage of the wave through the sample;
   c. means for measuring the time of flight for the wave through the sample, between transmission and reception of the wave;
   d. means for calculating the attenuation of the strength of the wave during the time of flight of the wave; and,
   e. means for calculating from the time of flight and attenuation an identification parameter dependent on the type or concentration of the target species in the sample, said means for calculating being independent of the distance travelled by the wave through the sample.

23. Apparatus according to claim 22, wherein the means for transmitting the wave of ultrasonic vibration is a transducer.

24. Apparatus according to claim 22, wherein the means for calculating the attenuation of the strength of the wave, and the means for calculating the identification parameter, comprise a computer.

25. Apparatus according to claim 22, additionally comprising a database of known identification parameters, for known types or concentrations of species, with which an identification parameter calculated using the apparatus may be compared.

26. Apparatus according to claim 25, wherein the database is a computer database.

27. Apparatus according to claim 25, wherein the database includes calibration spectra for target species, showing the variation of the identification parameter for each target species with the frequency of ultrasonic vibration passing through a sample containing the species or with the concentration of the target species in a sample.

28. Apparatus according to claim 25 wherein the database includes index or deviation parameters for known types or concentrations of species.

* * * * *